(12) United States Patent
Marosfoi et al.

(10) Patent No.: US 11,654,011 B2
(45) Date of Patent: May 23, 2023

(54) SYSTEM AND METHODS FOR TREATING NEUROVASCULAR COMPRESSION

(71) Applicant: University of Massachusetts, Boston, MA (US)

(72) Inventors: Miklos Marosfoi, Shrewsbury, MA (US); Matthew Gounis, Shrewsbury, MA (US); Ajay K. Wakhloo, Weston, MA (US)

(73) Assignee: University of Massachusetts, Boston, MA (US)

( * ) Notice: Subject to any disclaimer, the term of this patent is extended or adjusted under 35 U.S.C. 154(b) by 121 days.

(21) Appl. No.: 16/616,088

(22) PCT Filed: May 30, 2018

(86) PCT No.: PCT/US2018/035133
§ 371 (c)(1),
(2) Date: Nov. 22, 2019

(87) PCT Pub. No.: WO2018/222717
PCT Pub. Date: Dec. 6, 2018

(65) Prior Publication Data
US 2020/0146804 A1 May 14, 2020

Related U.S. Application Data

(60) Provisional application No. 62/512,289, filed on May 30, 2017.

(51) Int. Cl.
*A61F 2/06* (2013.01)
*A61F 2/90* (2013.01)
(Continued)

(52) U.S. Cl.
CPC ............... *A61F 2/06* (2013.01); *A61F 2/90* (2013.01); *A61F 2/95* (2013.01);
(Continued)

(58) Field of Classification Search
CPC ...... A61F 2/06; A61F 2/82; A61F 2/86; A61F 2/88; A61F 2/90; A61F 2/848; A61F 2/95;
(Continued)

(56) References Cited

U.S. PATENT DOCUMENTS 9,999,413 B2 * 6/2018 Hebert ............. A61B 17/12118
10,433,847 B2 * 10/2019 Florescu ............ A61B 17/3468
(Continued)

FOREIGN PATENT DOCUMENTS

EP 2 805 695 A1 11/2014
KR 20140101148 * 1/2013
(Continued)

OTHER PUBLICATIONS

English Translation of KR20140101148A (Year: 2013).*
(Continued)

*Primary Examiner* — Keri J Nelson
*Assistant Examiner* — Rebecca Lynee Zimmerman
(74) *Attorney, Agent, or Firm* — Hamilton, Brook, Smith & Reynolds, P.C.

(57) ABSTRACT

The invention is directed to a system and methods for treating neurovascular compression. Certain preferred embodiments of the invention generally comprise an apparatus having an elongated body portion including a proximal anchor element and distal anchor element. The apparatus also may include one or more marker elements to facilitate placement of the apparatus by the user. The apparatus may be configured to permit the user, after insertion and deployment of the apparatus in a blood vessel, to move the blood vessel so that the blood vessel is no longer in contact with and compressing a nerve or other parts of the nervous system.

21 Claims, 10 Drawing Sheets

(51) Int. Cl.
*A61F 2/95* (2013.01)
*A61F 2/848* (2013.01)
*A61M 25/09* (2006.01)
*A61M 25/00* (2006.01)

(52) U.S. Cl.
CPC .............. *A61F 2002/8486* (2013.01); *A61F 2210/0014* (2013.01); *A61F 2210/0071* (2013.01); *A61F 2250/0098* (2013.01); *A61M 25/09* (2013.01); *A61M 2025/0042* (2013.01)

(58) Field of Classification Search
CPC ........... A61F 2002/8486; A61M 25/09; A61M 2025/0042
See application file for complete search history.

(56) References Cited

U.S. PATENT DOCUMENTS

| | | | |
|---|---|---|---|
| 2004/0059407 A1 | 3/2004 | Escamilla et al. | |
| 2004/0260384 A1* | 12/2004 | Allen | A61F 2/88 623/1.12 |
| 2006/0025845 A1 | 2/2006 | Escamilla et al. | |
| 2006/0259127 A1 | 11/2006 | Tolomeo et al. | |
| 2013/0211489 A1* | 8/2013 | Makower | A61F 2/06 623/1.2 |
| 2014/0200655 A1 | 7/2014 | Webler, Jr. et al. | |
| 2015/0351912 A1 | 12/2015 | Konstantino et al. | |
| 2016/0242908 A1 | 8/2016 | Kim et al. | |
| 2017/0165048 A1* | 6/2017 | Chung | A61F 2/06 |
| 2018/0318115 A1* | 11/2018 | Chinubhai | A61F 2/852 |

FOREIGN PATENT DOCUMENTS

| | | |
|---|---|---|
| KR | 20140101148 A | 8/2014 |
| WO | WO2017/047819 A1 | 3/2017 |
| WO | WO2017/099467 A1 | 6/2017 |

OTHER PUBLICATIONS

International Preliminary Report on Patentability for International Application No. PCT/US18/35133 entitled "System and Methods for Treating Neurovascular Compression," dated Dec. 12, 2019.
Extended European Search Report for European Application No. 18810792.4 entitled "System and Methods for Treating Neurovascular Compression," dated Jan. 26, 2021.
International Search Report and Written Opinion for International Application No. PCT/US18/35133 entitled "System and Methods for Treating Neurovascular Compression," dated Oct. 16, 2018.

* cited by examiner

SYSTEM AND METHODS FOR TREATING NEUROVASCULAR COMPRESSION

CROSS-REFERENCE TO RELATED APPLICATIONS

This application is the U.S. National Stage of International Application No. PCT/US2018/035133, filed May 30, 2018, which designates the U.S., published in English, and claims to the benefit of U.S. Provisional Application No. 62/512,289, filed May 30, 2017. The entire teachings of the above applications are incorporated herein by reference.

FIELD OF INVENTION

The present invention relates generally to treating medical conditions. More specifically, the invention relates to a system and methods of treating the vascular compression of nerves.

BACKGROUND OF THE INVENTION

Every year, neurovascular compression—a condition that develops in the area in which a blood vessel contacts and compresses a nerve—affects tens of thousands of new patients. The most widely described and examined disease that may result from neurovascular compression is Trigeminal Neuralgia ("TN"). TN affects approximately 26,000 new patients each year. Although the underlying cause of TN is heterogenic, neurovascular compression is thought to be the cause in more than 50% of cases. Most often, TN develops because cranial nerve V—which sends sensory information regarding touch and pressure to the brain from the face and forehead, jaw and gums, and the eye area—is compressed by an adjacent vascular structure, which in many instances, is the Superior Cerebellar Artery. In the other cases, the symptoms may be related to other possible underlying pathologies including multiple sclerosis, inflammation, and tumor compression, or be of an idiopathic origin. Although the symptoms may vary, the most common complaint from patients with TN is a sudden, recurrent hemi-facial stabbing sensation—that may last from seconds to minutes and occur up to 120 times a day—and produce excruciating pain for the patient.

Currently, the preferred option of treatment for nerve compression symptoms is a prescribed medication regimen. The most widely prescribed medication for symptoms of nerve compression is a non-steroidal, anti-inflammatory drug and/or anti-epileptic drugs, such as carbamazepine, oxcarbazepine, or phenytoin. Unfortunately, current medication regimens have a low long-term efficacy rate (50% reoccurrence of symptoms after 3 years) and include side effects that may significantly alter a patient's quality of life. In addition, the initial effectiveness of a medication regimen may decline over time.

One alternative to a prescribed medication regimen is nerve decompression surgery such as, microvascular decompression, or percutaneous nerve destruction including radiofrequency thermo-coagulation, balloon compression, or percutaneous glycerol rhizolysis. While these surgical procedures may produce the highest treatment efficacy compared to other currently available treatment options, these procedures are highly invasive and may have an approximately 5% peri-procedural complication rate and a long-term symptom recurrence rate as high as 25%.

An alternate procedure, known as Gamma-knife surgery—a tool for targeted irradiation of the nerve (resulting in destruction of the nerve over time)—has a delay in pain relief onset, approximately 1.5 month, and, as with medical treatment, only 30% of the patients remain pain free at 5 years post treatment.

Accordingly, there is a need for an efficacious system and methods of treating neurovascular compression that has a lower complication rate, reduced side effects, and is less invasive than current approaches. The present invention satisfies this need.

SUMMARY OF THE INVENTION

Certain embodiments of the invention are directed to a system and methods intended to relieve neurovascular compression resulting from the contact of a blood vessel with a nerve. Certain embodiments of the system include the use of an apparatus having an elongated body portion. Other certain embodiments of the invention may include also an anchor element disposed on at least one end of the elongated body portion. According to certain preferred embodiments of the inventive methods, the apparatus may be inserted and deployed within a blood vessel using current endovascular techniques (e.g. microcatheter insertion) in order to change the architecture of (e.g. straighten out a curvature) and reposition the blood vessel to relieve vascular compression of the nerve.

Advantageously, certain preferred embodiments of the present invention employ a minimally invasive intravascular placement method that may allow for the precise deployment of the nerve decompression apparatus. Certain embodiments of the present invention may be used to treat a variety of nerve disorders including TN, tinnitus, brain stem compression, and vascular compression that may affect the brain parenchyma, brain stem, or spinal cord.

Moreover, in addition to relieving vascular compression of a nerve, the mechanical restructuring of a blood vessel according to certain preferred embodiments of the present invention may also reduce or eliminate a phenomenon known as blood vessel pulsation. Pulsation—which may be caused by the normal cardiovascular pulsing of the blood vessel in contact with a nerve—may not only cause damage to the nerve but may also be extremely painful. The mechanical restructuring of a blood vessel and the resultant reduction of blood vessel pulsation may allow the decompressed nerve time to regenerate or recover from the compression. This may lead to a higher longer-term efficacy rate of treatment, as well as a longer-term symptom relief.

Additionally, because the decompression procedure according to certain preferred embodiments of the invention may use a minimally invasive endovascular insertion route, the procedure may result in shorter recovery time, and fewer complications, such as local and systemic infections and damage to other cranial nerves, which may occur during or after open surgery.

Certain preferred embodiments of the invention may include the use of an apparatus that may be advantageously configured to include a body portion comprising a single wire, a plurality of wires forming a braided wire, or a plurality of wires forming a tubular wire mesh pattern similar to a stent and having a central lumen.

Some preferred embodiments of the apparatus also may include an anchor element disposed at one or both ends of the body portion. The anchor element may be sized and shaped to be inserted into a blood vessel, and, upon expansion of the anchor element, securely contact the inner wall of a blood vessel to prevent the apparatus from dislodging during the vessel restructuring procedure. Certain preferred embodiments of the anchor element may be spherical or oblong in shape. Other preferred embodiments may have a flared or open anchor element. The anchor element also may be of a self-expanding material that may facilitate positioning and deployment of the apparatus.

Certain preferred embodiments of the apparatus may include one or more marker elements, which may aid the user in guiding the apparatus into a desired position within a blood vessel when using radiographic or other visualization and display techniques (e.g. x-rays). Preferably, the one or more marker elements may be positioned on an anchor element and/or positioned on the body portion of the apparatus. In some embodiments of the apparatus, the one or more marker elements may be positioned on both the anchor element and the body portion.

One preferred method of treating vascular compression according to the invention may include the use of a guidewire to position a microcatheter within a blood vessel at a site of vascular nerve compression, removing the guidewire from the microcatheter, and inserting a preferred embodiment of an apparatus of the invention into the microcatheter. The apparatus may then be positioned at the site of vascular compression, and the microcatheter may then be withdrawn from the site of vascular compression to allow the apparatus to deploy and contact the inner wall of the blood vessel. The insertion and deployment of the apparatus may result in a change in the geometry of the blood vessel and may reposition the blood vessel away from, and no longer in contact with the compressed nerve.

In certain embodiments of the method of the invention, an apparatus may be test-fitted, that is, the apparatus may initially be positioned at a site of vascular nerve compression, and the apparatus may then either be repositioned or replaced (e.g. the apparatus has too wide of a diameter to fit into the site of vascular nerve compression, or the apparatus is too rigid to fit into the curvature of a blood vessel) with a different apparatus as needed. In some instances, it may be advantageous to use an apparatus having marker elements to aid the user in positioning the apparatus at the desired location. The present invention and its attributes and advantages will be further understood and appreciated with reference to the detailed description below of presently contemplated embodiments, taken in conjunction with the accompanying drawings.

BRIEF DESCRIPTION OF THE DRAWINGS

The preferred embodiments of the invention will be described in conjunction with the appended drawings provided to illustrate and not to the limit the invention, where like designations denote like elements, and in which.

DETAILED DESCRIPTION OF THE INVENTION

The present invention is directed to a system and methods for treating vascular compression of nerves. More specifically, certain preferred embodiments of an apparatus of the invention may be inserted and deployed at a site of vascular compression and may change the geometry of a blood vessel that is compressing a nerve such that the blood vessel and the nerve are no longer in contact.

Figure 1:
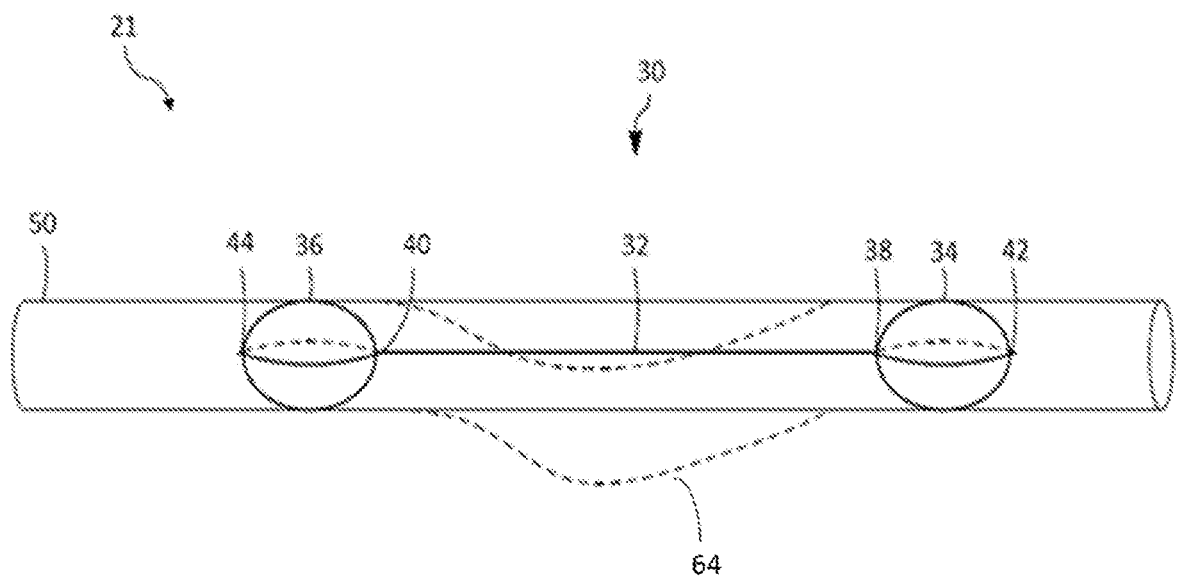
FIG. 1 illustrates a schematic view of a preferred embodiment of the invention.

FIG. 1 illustrates one preferred embodiment of a system 21 according to the present invention which includes an apparatus 30 positioned in a curved blood vessel 64 that may be in contact with a nerve. Apparatus 30 includes an elongated body portion 32 including a proximal anchor element 34 disposed at the proximal end 38 of the body portion 32 and a distal anchor element 36 disposed at the distal end 40 of the body portion 32. The distal anchor element 36 may be positioned distally to the blood vessel curvature. The embodiment of the apparatus 30 illustrated in FIG. 1 also may include a proximal marker element 42 and a distal marker element 44. After insertion and deployment of the apparatus 30, the geometry of blood vessel 50 is changed so that the blood vessel is no longer distended.

Figure 2A:
FIG. 2A illustrates a view of certain embodiments of a body portion of the invention including a wire body.
Figure 2B:
FIG. 2B illustrates a view of certain embodiments of a body portion of the invention including a braided body.
Figure 2C:
FIG. 2C illustrates a view of certain embodiments of a body portion of the invention including a mesh wire body.

As further illustrated in FIG. 2A-C, certain preferred embodiments of the body portion 32 may generally comprise one or more wires. As shown in FIG. 2A, some preferred embodiments of the body portion may comprise a single wire 32A. In other certain preferred embodiments of the invention shown in FIG. 2B, the body portion may comprise at least two wires wrapped about one another to form a braided wire 32B. In additionally preferred embodiments of the invention shown in FIG. 2C, the body portion may comprise a wire mesh pattern of a plurality of thin wires, much like a stent, forming a tube having a tube structure 32C that defines a central lumen.

Embodiments of the body portion 32 of the apparatus may be constructed of a metal or metal alloy including stainless steel, titanium, nickel titanium, nitinol, tantalum, gold, cobalt-chromium, platinum, palladium, iridium, or other metals. In certain preferred embodiments of the invention, the body portion may be constructed of nitinol. Nitinol possess unique shape memory properties that may facilitate delivery though small microcatheters and displays self-expanding properties at body temperature.

Further embodiments also may be constructed of a biocompatible polymer including polyurethanes, polyetherurethanes, polyesterurethanes, silicone, thermoplastic elastomers (such as C-Flex®), polyether-amide thermoplastic elastomer (such as Pebax®), fluoroelastomers, fluorosilicone elastomer, styrene-butadiene rubber, butadiene-styrene rubber, polyisoprene, neoprene (polychloroprene), ethylenepropylene elastomer, chlorosulfonated polyethylene elastomer, butyl rubber, polysulfide elastomer, polyacrylate elastomer, nitrile rubber, a family of elastomers composed of styrene, ethylene, propylene, aliphatic polycarbonate polyurethane, polymers augmented with antioxidants, polymers augmented with image enhancing materials, polymers having a proton (H+) core, polymers augmented with protons (H+), butadiene and isoprene (such as Kraton®) and polyester thermoplastic elastomer (such as Hytrel®), polyethylene, polylactic acid, polyglycolic acid, poly(lactic-co-glycolic acid or other biocompatible polymer. In certain preferred embodiments, the biocompatible polymer metal may form a coating over at least a portion of a metal body portion.

In other certain embodiments of the invention, the body portion 32 may be configured to have a certain rigidity and/or shape. For example, an embodiment with a certain rigidity and shape may be advantageous in straightening out a curvature or otherwise affect the geometry of a blood vessel upon insertion of an apparatus into a desired position. In other situations, embodiments of the apparatus may be advantageously configured to have a certain rigidity (e.g. less rigidity) and shape that may allow the apparatus to enter a narrow blood vessel or enter a blood vessel with a more severe curvature.

Several factors may control the rigidity of the apparatus. These factors may include, for example, the number of wires in a braided apparatus, the thickness of the wires, and the various materials used to construct the wires. Therefore, the invention permits the user to choose the materials and shape of the apparatus—based upon the required remodeling of the blood vessel and the position of the compression site—to have a certain rigidity to achieve the desired result. In some embodiments, the apparatus may have a rigidity of about 0.5 N/mm bending moment.

The body portion 32 may be sized and shaped to be inserted into a blood vessel. Depending on the diameter of the blood vessel at the application site, certain embodiments of the apparatus may have a body portion 32 with a diameter of about 0.01 mm to about 4 mm. Certain preferred embodiments of the apparatus, such as a wire-like apparatus comprising a single wire, may have a body portion diameter of about 0.01 mm to about 1 mm and may be used at a narrower site of compression in the blood vessel. A more stent-like or braided apparatus comprising a plurality of wires may have a body portion diameter of about 1.0 mm to about 4.0 mm and more preferably, about 1.0 to about 2.5 mm, and may be used at a less narrow site of compression in a blood vessel.

In certain embodiments of the apparatus, the length of the body portion 32 may be configured to be the approximate length of a curvature in a blood vessel that the user wishes to remodel or straighten out. In certain preferred embodiments of the apparatus, the body portion 32 may be about 5 mm to about 20 mm in length.

An anchor element 34, 36 generally may be disposed at one end, and preferably at each end 38, 40 of the body portion 32. At least one of the anchor elements may be positioned distally to the blood vessel curvature. In some embodiments of the invention, anchor elements 34, 36 may fix the apparatus in a specific location through, for example, contact with the inner wall of a blood vessel. Anchor elements 34, 36 may allow unimpeded blood flow through the blood vessel after the apparatus is positioned. Preferably, anchor elements 34, 36 may have a diameter of about 1 mm to about 5 mm depending on the diameter of the blood vessel at the site of compression. Further embodiments of anchor elements 34, 36, such as a flared or open-ended anchor element as discussed below, may have a length of about 3 mm to about 5 mm.

Figure 3A:
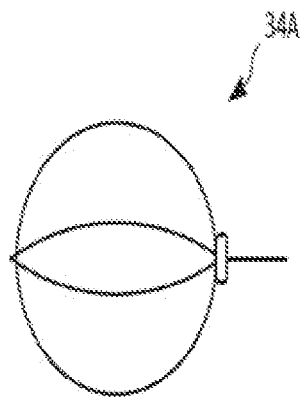
FIG. 3A illustrates a cross-sectional view of certain embodiments of a proximal or distal anchor element of the invention including a spherical or oval anchor.
Figure 3B:
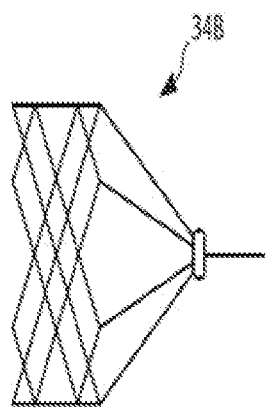
FIG. 3B illustrates a cross-sectional view of certain embodiments of a proximal or distal anchor element of the invention including a mesh anchor.
Figure 3C:
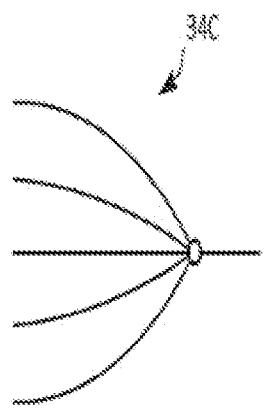
FIG. 3C illustrates a cross-sectional view of certain embodiments of a proximal or distal anchor element of the invention including a cone-shaped anchor.

FIG. 3A-C illustrate certain embodiments of anchor elements 34, 36 that may be sized and shaped to deploy within a blood vessel and contact the inner wall of the blood vessel to secure the apparatus in position. More specifically, as shown in FIG. 3A, embodiments of the anchor elements 36A may include one or more wires (e.g., 2, 3, 4, 5, or 6 wires) originating from the proximal or distal end of the body portion and may connecting or cross at a connection point opposite the proximal or distal end to form a spherical or oblong shape. Further embodiments of an anchor element shown in FIG. 3B may include a plurality of wires originating from a proximal or distal end of the body portion and expanding radially for a distance to form a mesh structure 36B. Other certain embodiments of an anchor element shown in FIG. 3C may comprise a plurality of wires that may expand radially from a proximal or distal end of a body portion to form an open-ended cone-like structure 36C (i.e., a flared end). In preferred embodiments of the invention, the anchor elements 34, 36 may be constructed of a self-expanding material (e.g., nitinol), however, the anchor elements also may be constructed of any one of the biocompatible metals or polymers disclosed herein.

An embodiment of a certain anchor element may be chosen for use depending on both the amount of curvature of a blood vessel at the target site and the geometry of the blood vessel distal to the target site. For example, a spherical or oblong anchor element may be less rigid (i.e. more flexible) than a mesh-type anchor element due to the fewer number of wires that form the anchor element. Accordingly, it may be advantageous to use a spherical or oblong anchor element in situations of extreme blood vessel curvature at the target site (so that the anchor element may pass through the curvature) and/or the geometry of the blood vessel distal to the target site also is more curved. In contrast, a mesh-type anchor—being more rigid due to the number of wires forming the mesh—may be better suited for use when the blood vessel curvature at the target site is minimal and/or the geometry of the blood vessel distal to the target site is less curved.

As shown above in reference to in FIG. 1, certain embodiments of the invention may also include one or more marker elements 42, 44. Marker elements 42, 44 may aid in the visualization of an apparatus in vivo, such as during placement of the apparatus at a compression site within a blood vessel, when using radiographic or similar means of observation and display. Marker elements 42, 44 may include radiopaque agents such as tantalum, barium, bismuth, or other metals such as gold, platinum, to increase radiopacity. These radiopaque agents may be bonded to the structure of the apparatus such as by rubbing, bonding, or adhering the agent to the apparatus.

In some embodiments of the invention, marker elements 42, 44 may be disposed at various positions along the length of the apparatus including the body portion 32 and anchor element 34, 36. In a preferred embodiment of the invention, marker elements 42, 44 may be disposed at the outer edge of anchor element 34, 36 such that a user may visually recognize the boundaries of the apparatus during deployment. For example, marker elements may be disposed along the uppermost or bottommost portion of anchor element 34, 36 to help visualize the contact of the anchor element with the inner wall of a blood vessel. Other embodiments of the invention, such as an open-ended mesh 36B and stent-like apparatus 36C, may include a plurality of marker elements disposed about the anchor element and/or a proximal end or a distal end of the body portion. A closed-ended apparatus—for example, an apparatus having a wire-like body portion 32B without any anchor elements—may have a single marker element disposed at a proximal end or distal end of the body portion.

Certain embodiments of the invention may permit a user to change the geometry of a blood vessel compressing a nerve. Exemplary methods of changing the geometry of a blood vessel may include the use of a guidewire disposed within a microcatheter sized and shaped to house and deliver the microcatheter to a target site in a blood vessel that is compressing a nerve. Initially, a user may measure both the length of the curvature of the target blood vessel, as well as the diameter of the blood vessel in order to select an embodiment of an apparatus of the invention having sufficient length and rigidity to change the geometry of the blood vessel, as well as the appropriate anchor element to secure the apparatus in its final position.

Figure 4A:
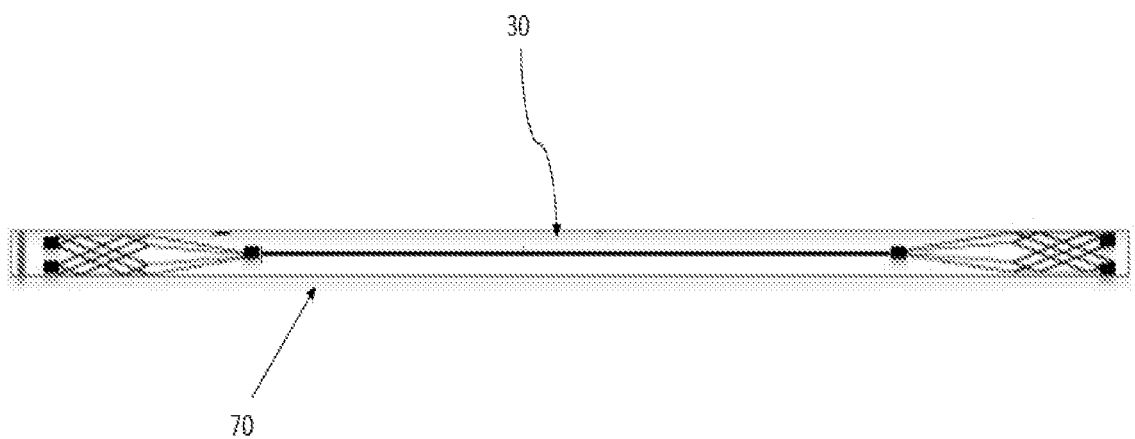
FIG. 4A illustrates a schematic view of an embodiment of the invention housed within a microcatheter prior to deployment at a target site.
Figure 4B:
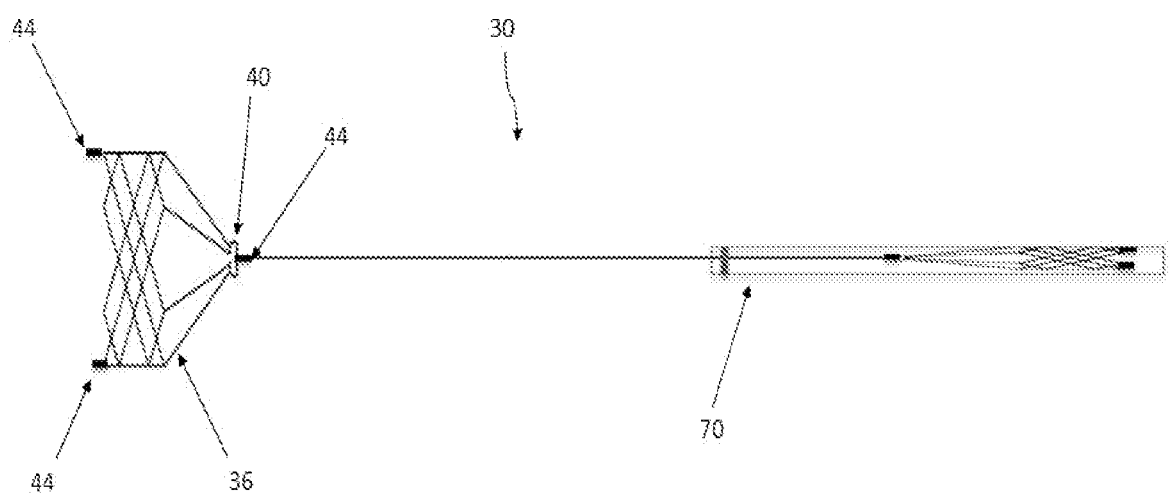
FIG. 4B illustrates a schematic view of a partial deployment of an embodiment of the invention at a target site.
Figure 4C:
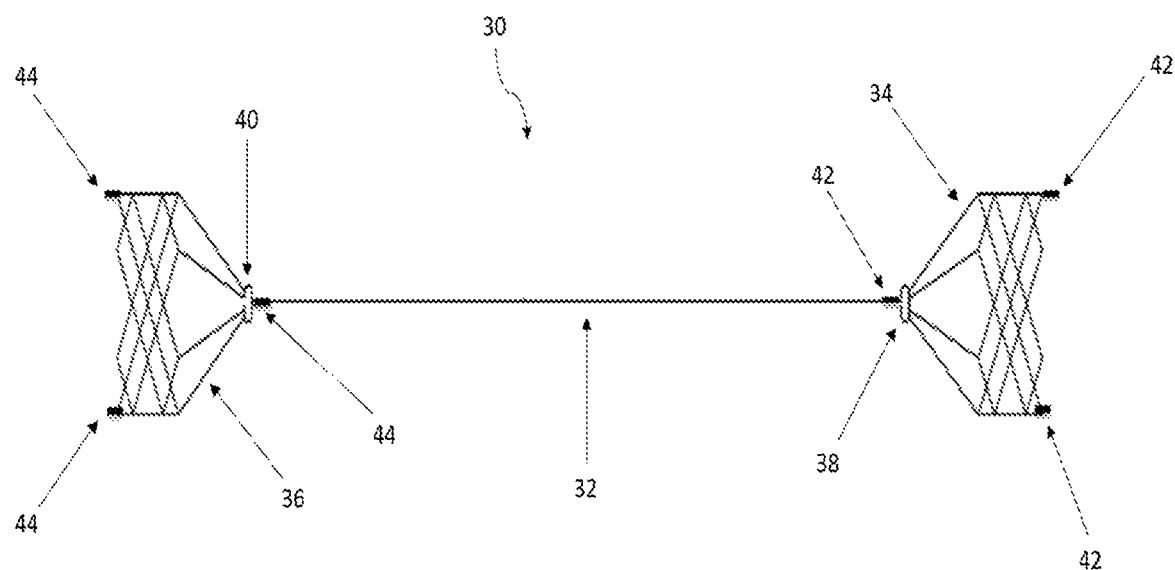
FIG. 4C illustrates a schematic view of the full deployment of an embodiment of the invention at a target site.

As illustrated in FIG. 4A-4C, using a guidewire, a microcatheter 70 may be delivered distal to the target site (i.e. a curvature of a blood vessel contacting a nerve). Once the microcatheter 70 is in position, the guidewire may be withdrawn from the microcatheter 70 and an embodiment of the apparatus 30 of the invention inserted into the microcatheter 70 and advanced to the tip of the microcatheter 70 (FIG. 4A). After the apparatus 30 is in position, as determined by, for example, visualization and display of the marker elements 42, 44, the microcatheter 70 may be withdrawn from the site of compression to allow the anchor element 36 at the distal end 40 of apparatus 30 to self-expand and contact the vessel walls (FIG. 4B). The insertion and deployment of the distal end 40 of the apparatus may cause a change in the geometry of the vessel (e.g. change a curve in a vessel to a more linear conformation), thereby relieving nerve compression by moving the blood vessel away from the nerve. Once it is determined that the desired change in geometry of the blood vessel is achieved, the apparatus 30 may be completely deployed and anchored into position as the microcatheter 70 is fully withdrawn from the blood vessel (FIG. 4C). Anchoring of the apparatus 30 into position may ensure the change in geometry of the blood vessel persists over time.

In certain situations, the initial positioning, or the amount of change in geometry of the blood vessel caused by the apparatus may be suboptimal. In such cases, the apparatus—prior to full deployment and detachment from the microcatheter—may be resheathed into the microcatheter and either repositioned, or the entire apparatus withdrawn and replaced with a new apparatus with the desired properties (e.g. rigidity) to achieve the desired results.

Figure 5A:
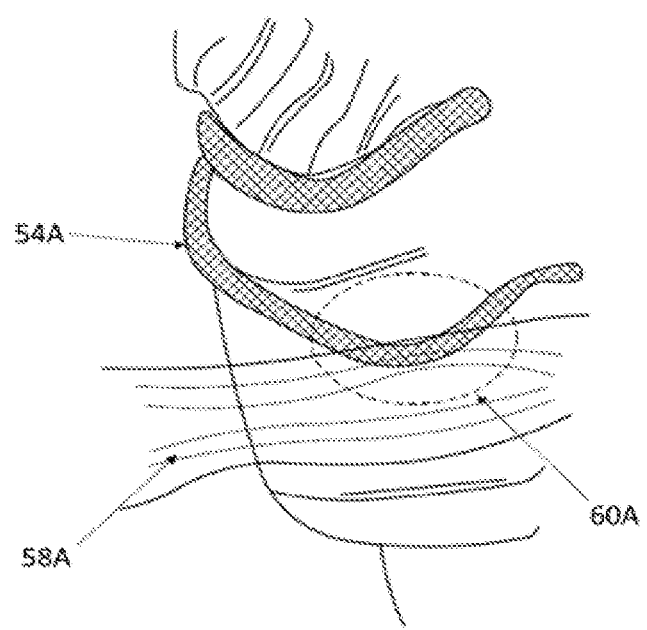
FIG. 5A illustrates a view of a brain stem depicting neurovascular compression prior to treatment with an embodiment of the invention.
Figure 5B:
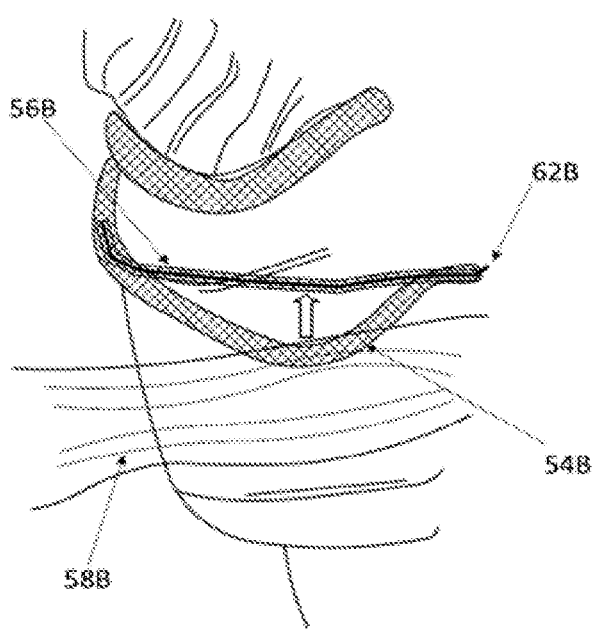
FIG. 5B illustrates a brain stem after the deployment of an embodiment of the invention and repositioning of the blood vessel to a non-compressing position away from the nerve.

FIG. 5A-B and FIG. 6A-B illustrate the use of an embodiment of an apparatus of the invention to relieve vascular compression of a nerve, such as, for example, the trigeminal nerve. In FIG. 5A, the normal anatomical geometry of the Superior Cerebellar Artery ("SCA") 54A has changed such that the SCA has come onto contact 60A with and causing compression of the trigeminal nerve 58A. FIG. 5B illustrates the same SCA vessel after insertion and deployment of an embodiment of an apparatus 62B of the present invention within the distended SCA loop 54B to change the geometry of the vessel such that the SCA no longer compresses 56B the Trigeminal nerve 58B.

Figure 6A:
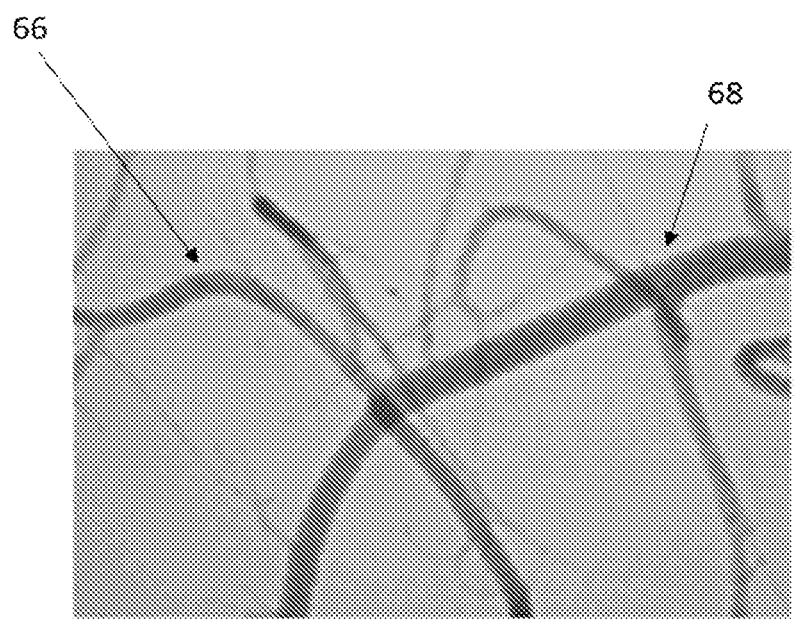
FIG. 6A illustrates in vivo imaging of the use of an embodiment of the invention to change the geometry of a blood vessel that more specifically shows the geometry of a blood vessel prior to insertion and placement of an embodiment of an apparatus within a blood vessel.
Figure 6B:
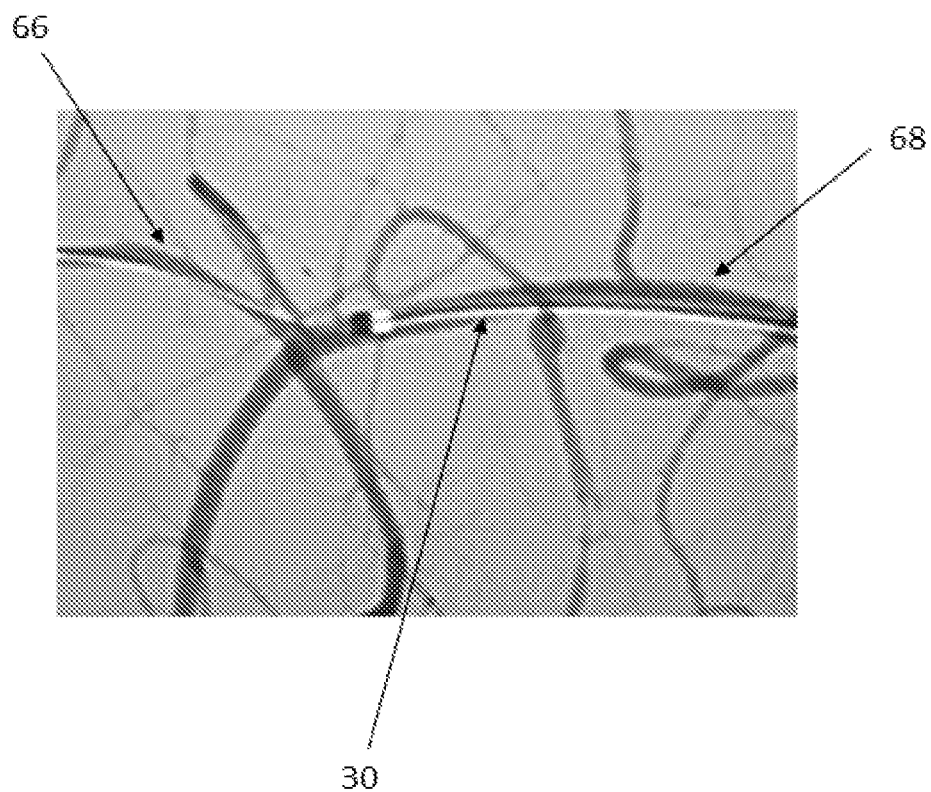
FIG. 6B illustrates in vivo imaging of the same blood vessel in FIG. 6A after insertion and deployment of an embodiment of an apparatus of the invention to change the geometry of the blood vessel.

FIG. 6A-B illustrate the in vivo use of an embodiment of the invention. FIG. 6A shows a target vessel having a downward curve or angle 68 at the origin of the vessel and an upward curve 66 distal to the origin of the vessel. In FIG. 6B, an embodiment of an apparatus of the invention is shown in position within the target vessel where the vascular geometry has been changed to decrease the angle of the downward curve 68 and to straighten the distal curve 66.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An apparatus configured to change a geometry of a blood vessel in contact with a nerve, the apparatus comprising:
   a body portion having a proximal end and a distal end;
   an anchor element disposed on at least one of said proximal end and said distal end; and
   one or more marker elements disposed on said body portion;
   said body portion comprising at least two wires wrapped about one another to form a braided wire, the body portion being sized and shaped to change the geometry of the blood vessel upon insertion of the apparatus into the blood vessel to no longer contact the nerve, and being configured to have a rigidity and a length, the rigidity and length selected based on a length of a curvature in the blood vessel and a diameter of the blood vessel, the rigidity controlled by one or more of the number of wires of the braided wire, a thickness of the wires, and a material of the wires, the rigidity being sufficient to retain the changed geometry of the blood vessel with the apparatus positioned therein and reduce or eliminate blood vessel pulsation.

2. The apparatus of claim 1, wherein said apparatus is constructed of a biocompatible polymer.

3. The apparatus of claim 1, wherein said apparatus is constructed of a biocompatible metal selected from the group consisting of nitinol, stainless steel, and cobalt-chromium alloy.

4. The apparatus of claim 1, wherein said anchor element is constructed of a self-expanding material.

5. The apparatus of claim 1, wherein said anchor element includes a flared end or open end.

6. The apparatus of claim 1, wherein said anchor element is disposed on each of said proximal end and said distal end.

7. A method for treating vascular nerve compression comprising:

using a guidewire to position a microcatheter within a blood vessel at a site of the vascular nerve compression;

withdrawing the guidewire from the microcatheter and inserting an apparatus of claim 1 into the microcatheter;

positioning the apparatus at the site of the vascular nerve compression;

withdrawing the microcatheter from the site of vascular nerve compression to deploy the apparatus; and repositioning the blood vessel using the apparatus to no longer contact a nerve and reduce the vascular nerve compression.

8. The method of claim 7, wherein
said anchor element is disposed on each of said proximal end and said distal end of said body portion, wherein said anchor element is configured to secure the apparatus within the blood vessel after the insertion of the apparatus.

9. The method of claim 7, wherein said anchor element is constructed of a self-expanding material.

10. The method of claim 7, wherein the apparatus further comprises at least one marker element disposed on said anchor element.

11. The method of claim 7, wherein the method further comprises repositioning the apparatus prior to withdrawing the microcatheter.

12. The method of claim 7, wherein the nerve is a cranial nerve.

13. The method of claim 12, wherein the cranial nerve is a trigeminal nerve.

14. The method of claim 7, wherein the method further comprises mechanically restructuring the blood vessel using the apparatus to reduce blood vessel pulsation.

15. The method of claim 7, wherein the method further comprises measuring a length of curvature of the blood vessel and a diameter of the blood vessel to select an apparatus having sufficient length and rigidity to change the geometry of the blood vessel.

16. The apparatus of claim 1, wherein the body portion is configured to have a rigidity of about 0.5 N/mm bending moment.

17. The apparatus of claim 1, wherein the body portion is configured to have a length of approximately the length of the curvature in the blood vessel.

18. The apparatus of claim 1, wherein the body portion is configured to have a length of about 5 mm to about 20 mm.

19. The apparatus of claim 1, wherein the body portion is configured to have a diameter based on the diameter of the blood vessel, the body portion diameter being about 1.0 mm to about 4.0 mm.

20. An apparatus configured to change a geometry of a blood vessel in contact with a nerve, the apparatus comprising:

a body portion having a proximal end and a distal end; and one or more marker elements disposed on said body portion;

said body portion comprising at least two wires wrapped about one another to form a braided wire, the body portion being sized and shaped to change the geometry of the blood vessel upon insertion of the apparatus into the blood vessel to no longer contact the nerve, and being configured to have a rigidity of about 0.5 N/mm bending moment and a length, the rigidity and length selected based on a length of a curvature in the blood vessel and a diameter of the blood vessel, the rigidity controlled by one or more of the number of wires of the braided wire, a thickness of the wires, and a material of the wires, the rigidity being sufficient to retain the changed geometry of the blood vessel with the apparatus positioned therein and reduce or eliminate blood vessel pulsation.

21. A method for treating vascular nerve compression comprising:

using a guidewire to position a microcatheter within a blood vessel at a site of the vascular nerve compression;

withdrawing the guidewire from the microcatheter and inserting an apparatus into the microcatheter;

positioning the apparatus at the site of the vascular nerve compression;

repositioning the apparatus prior to withdrawing the microcatheter;

withdrawing the microcatheter from the site of vascular nerve compression to deploy the apparatus; and repositioning the blood vessel using the apparatus to no longer contact a nerve and reduce the vascular nerve compression;

wherein the apparatus comprises:

a body portion having a proximal end and a distal end; and one or more marker elements disposed on said body portion;

said body portion comprising at least two wires wrapped about one another to form a braided wire, the body portion being sized and shaped to change the geometry of the blood vessel upon insertion of the apparatus into the blood vessel to no longer contact the nerve, and being configured to have a rigidity and a length, the rigidity and length selected based on a length of a curvature in the blood vessel and a diameter of the blood vessel, the rigidity controlled by one or more of the number of wires of the braided wire, a thickness of the wires, and a material of the wires, the rigidity being sufficient to retain the changed geometry of the blood vessel with the apparatus positioned therein and reduce or eliminate blood vessel pulsation.

* * * * *